(12) United States Patent
Compte et al.

(10) Patent No.: US 11,793,831 B2
(45) Date of Patent: Oct. 24, 2023

(54) TREATMENT AND PREVENTION OF INJURY DUE TO RADIATION EXPOSURE

(71) Applicant: MEDESIS PHARMA, Baillargues (FR)

(72) Inventors: Elsa Compte, Montpellier (FR); Patrick Maurel, Saint Vincent de Barbeyrargues (FR); Sophie Grives-Jerphagnon, Beaulieu (FR); Cyril Lavaud, Castelnau le lez (FR); Lorraine Benigno-Anton, Saturargues (FR); Jean-Claude Maurel, Baillargues (FR)

(73) Assignee: MEDESIS PHARMA, Baillargues (FR)

( * ) Notice: Subject to any disclaimer, the term of this patent is extended or adjusted under 35 U.S.C. 154(b) by 163 days.

(21) Appl. No.: 17/257,940

(22) PCT Filed: Jul. 5, 2019

(86) PCT No.: PCT/EP2019/068099
§ 371 (c)(1),
(2) Date: Jan. 5, 2021

(87) PCT Pub. No.: WO2020/008032
PCT Pub. Date: Jan. 9, 2020

(65) Prior Publication Data
US 2021/0315931 A1    Oct. 14, 2021

Related U.S. Application Data

(60) Provisional application No. 62/694,637, filed on Jul. 6, 2018.

(51) Int. Cl.
*A61K 33/32* (2006.01)
*A61P 39/00* (2006.01)
*A61K 9/107* (2006.01)
*A61K 47/10* (2017.01)
*A61K 47/14* (2017.01)
*A61K 47/24* (2006.01)
*A61K 47/28* (2006.01)

(52) U.S. Cl.
CPC ............ *A61K 33/32* (2013.01); *A61K 9/1075* (2013.01); *A61K 47/10* (2013.01); *A61K 47/14* (2013.01); *A61K 47/24* (2013.01); *A61K 47/28* (2013.01); *A61P 39/00* (2018.01)

(58) Field of Classification Search
CPC ...... A61K 33/32; A61K 9/1075; A61K 47/10; A61K 47/14; A61K 47/24; A61K 47/28; A61K 33/00; A61K 33/04; A61K 33/30; A61P 39/00; A61N 2005/1098
See application file for complete search history.

(56) References Cited

U.S. PATENT DOCUMENTS 9,452,136 B2    9/2016    Maurel

FOREIGN PATENT DOCUMENTS

WO    2011117333 A2    9/2011
WO    2017005899 A1    1/2017

OTHER PUBLICATIONS

International Search Report and Written Opinion for PCT/EP2019/068099, dated Sep. 26, 2019, 10 pages.

*Primary Examiner* — Jessica Worsham
(74) *Attorney, Agent, or Firm* — ARENTFOX SCHIFF LLP

(57) ABSTRACT

The disclosure relates to the treatment and/or prevention of radiation damage by administering a reverse micelle system.

17 Claims, 4 Drawing Sheets

TREATMENT AND PREVENTION OF INJURY DUE TO RADIATION EXPOSURE

CROSS-REFERENCE TO RELATED APPLICATIONS

This application is a U.S. National Stage of PCT/EP2019/068099, filed on Jul. 5, 2019, which claims the benefit of U.S. Provisional Application No. 62/694,637, filed on Jul. 6, 2018, the disclosures of which are hereby incorporated by reference in their entireties.

FIELD OF INVENTION

The disclosure relates to the treatment and/or prevention of injury due to radiation exposure by administering a reverse micelle system.

BACKGROUND

There have been significant advances in developing safe and effective radiation countermeasures for radiation injuries. However, only a few agents have been approved by the U.S. Food and Drug Administration (FDA) for human use in a non-clinical setting (e.g., dirty bomb, mass nuclear accident). For example, amifostine (Ethyol®) has not been approved by the FDA as radioprotector for the treatment of acute radiation syndrome (ARS), but only for a limited clinical use for patients undergoing radiotherapy or chemotherapy. Furthermore, amifostine is effective only when administered intravenously (i.v.) or subcutaneously (s.c.), and has a short-time window of effectiveness, and thus is not adapted to mass-casualty situation.

Two granulocyte colony stimulating factors (G-CSF) (Neupogen® and Neulasta) have been improved by the FDA as radiomitigators for the treatment of the hematopoietic sub syndrome of ARS (H-ARS). But these recombinant agents have limitations such as the need to be injected, multiple doses are required, and monitoring of side effects.

Several drugs are in different stages of evaluation by the FDA as radiation countermeasures for the prevention or treatment of ARS but so far none possesses all the requisite qualities to be an optimum radiation countermeasure, e.g., low toxicity, wide window of protection, stability under extreme conditions, easy to handle and to administer.

Superoxide dismutases (SOD) are enzymes that catalyze the dismutation of superoxide anions to oxygen and hydrogen peroxide and they are known for the involvement in antioxidant defense mechanisms (Huang, 2012). As the clinical application of manganese superoxide dismutase (Mn-SOD) is limited because of its short half-life, high molecular weight, and inability to cross cell membrane freely, other strategies such as SOD mimics have been developed (Miriyala, 2012). For example, AEOL10150, a metalloporphyrin Mn-SOD mimetic developed by Aeolus Pharmaceuticals, mitigates acute radiation-induced lung injury after multiple injections (MacVittie, 2017).

Greenberger and co-workers investigated a SOD-based gene therapy strategy.

They showed that Mn-SOD-plasmid in liposomes intravenously administered in rodents before ionizing radiation exposure has a potent efficacy to protect normal tissues (Epperly, 2008). In another study they showed that the daily administration of a diet rich in a mixture of micronutrient multivitamin and trace element including manganese, antioxidants and chemopreventive agents and optionally a mixture of fatty acids, does not ameliorate survival up to the thirty-day mark but, in animals surviving the acute effects of ionizing radiation, the diet ameliorates the radiation exposure-induced life shortening (Epperly, 2011 and US2014/0023701).

Murata and coworkers showed that manganese chloride, administered intraperitoneally does not protect against acute radiation injury of skin or crypt cells (Murata, 1995).

Manganese is not easy to administered due to its poor oral bioavailability and toxicity including progressive neurodegenerative damages with an associated motor dysfunction syndrome similar to that seen in Parkinson disease (Williams, 2012).

Several reverse micellar systems are known in the art. These systems require specific components and/or are directed to uses other than the treatment and/or prevention of radiation damage. For example, U.S. Pat. No. 9,592,218 discloses a reverse micelle system comprising at least one metal ion, a sterol, an acylglycerol, lecithin, alcohol and water, and methods for the treatment or improvement of symptoms of various diseases or disorders, but does not disclose the treatment and/or prevention of radiation damage.

U.S. Pat. No. 9,452,136 discloses a reverse micelle system comprising at least one nucleic acid, a sterol, an acylglycerol, a phospholipid or a sphingolipid, an alcohol and water, and methods for the treatment or improvement of symptoms of various diseases or disorders.

U.S. Pub. No. 2017/0035909 discloses a reverse micellar system comprising at least a chelating or sequestering agent, an acylglycerol, lecithin, an alcohol and water, and methods of one disease linked to the accumulation and/or overload of at least one radionuclide or metal.

WO 2017/005899 discloses the preparation of cyanobridged metal nanoparticles within a biocompatible reverse micellar system. The biocompatible reverse micellar system or the cyano-bridged metal nanoparticles comprised therein are used as a contrast agent and/or a diagnosis agent. The biocompatible reverse micellar system or the cyano-bridged metal nanoparticles comprised therein are used for substitution by and/or sequestering of radionuclide and/or metal cations.

Li and coworkers describe that beta-sitosterol had radioprotective effects on irradiated thymocytes by regulating the intracellular redox balances (decrease of ROS, increase of antioxidant enzyme activity such as SOD, catalase) (Li, 2007). The antioxidant effect was confirmed on irradiated rats by Moustafa and co-workers (Moustafa, 2017).

The foregoing publications are hereby incorporated by reference in their entireties.

Research progress in the radioprotective effect of superoxide dismutase. Huang X J, Song C X, Zhong C Q, Wang F S. Drug Discov Ther. 2012 August; 6(4):169-77.

Manganese superoxide dismutase, MnSOD and its mimics. Miriyala S, Spasojevic I, Tovmasyan A, Salvemini D, Vujaskovic Z, St Clair D, Batinic-Haberle I.Biochim Biophys Acta. 2012 May; 1822(5):794-814

AEOL 10150 Mitigates Radiation-Induced Lung Injury in the Nonhuman Primate: Morbidity and Mortality are Administration Schedule-Dependent. MacVittie T J, Gibbs A, Farese A M, Barrow K, Bennett A, Taylor-Howell C, Kazi A, Prado K, Parker G, Jackson W III. Radiat Res. 2017 March; 187(3):298-318.

Epperly M W, Dixon T, Wang H, Schlesselman J, Franicola D, Greenberger J S. Radiat Res. 2008 October; 170(4):437-43.

Antioxidant-chemoprevention diet ameliorates late effects of total-body irradiation and supplements radioprotection by MnSOD-plasmid liposome administration. Epperly M W, Wang H, Jones J A, Dixon T, Montesinos C A, Greenberger J S. Radiat Res. 2011 June; 175(6): 759-65.

Manganese chloride treatment does not protect against acute radiation injury of skin or crypt cells. Murata R, Nishimura Y, Hiraoka M, Abe M, Satoh M. Radiat Res. 1995 September; 143(3):316-9.

Toxicological Profile for Manganese. Williams M, Todd G D, Roney N, Crawford J, Coles C, McClure P R, Garey J D, Zaccaria K, Citra M. Atlanta (Ga.): Agency for Toxic Substances and Disease Registry (US); 2012 September Beta-sitosterol decreases irradiation-induced thymocyte early damage by regulation of the intracellular redox balance and maintenance of mitochondrial membrane stability. Li C R, Zhou Z, Lin R X, Zhu D, Sun Y N, Tian L L, Li L, Gao Y, Wang S Q. J Cell Biochem. 2007 Oct. 15; 102(3):748-58.

Beta-sitosterol upregulated paraoxonase-1 via peroxisome proliferator-activated receptor-γ in irradiated rats. Moustafa E M, Thabet N M. Can J Physiol Pharmacol. 2017 June; 95(6): 661-666.

US2014/0023701, US2017/0035909, U.S. Pat. Nos. 9,592,218 and 9,452,136, WO 2017/005899.

SUMMARY OF VARIOUS EMBODIMENTS

The disclosure provides for methods of treating a subject exposed to radiation and/or preventing radiation damage in a subject at risk for exposure to radiation comprising administering a reverse micellar system that comprises at least a sterol, 50 to 90% of acylglycerol, 1 to 20% of lecithin, ethanol, water, and optionally an active agent. In other embodiments, the active agent comprises at least one manganese ion. In other embodiments, the reverse micellar system does not include a nucleic acid or a chelating agent. The disclosure provides for a reverse micellar system that comprises at least a sterol, 50 to 90% of acylglycerol, 1 to 20% of lecithin, ethanol, water, and optionally an active agent, for use in the treatment of a subject exposed to radiation and/or preventing radiation damage in a subject at risk for exposure to radiation.

The disclosure also provides for a reverse micellar system comprising at least a sterol, 50 to 90% of acylglycerol, 1 to 20% of lecithin, ethanol and water, and wherein the reverse micellar system is free of metal and free of a chelator. In other embodiments, the reverse micellar system also does not include a nucleic acid. In a particular embodiment, the reverse micellar system consists of at least a sterol, 50 to 90% of acylglycerol, 1 to 20% of lecithin, ethanol and water. This reverse micellar system may be used in methods for treating a subject exposed to radiation and/or for preventing radiation damage in a subject at risk for exposure to radiation.

It is an object of this disclosure to provide compositions for treating and/or preventing cell, tissue or organ injury, in a living subject, due to exposure to ionizing radiation without any side effects. It is also an object to provide compositions that are easy to administer to a large population.

BRIEF DESCRIPTION OF THE FIGURES

FIG. 1: Post-TBI survival in CD1 Swiss mice after a 5.6 Gy dose irradiation at 0.16 Gy/min dose rate ($LD_{50/30}$). Treatments.

DETAILED DESCRIPTION OF VARIOUS EMBODIMENTS OF THE INVENTION

Figure 1A:
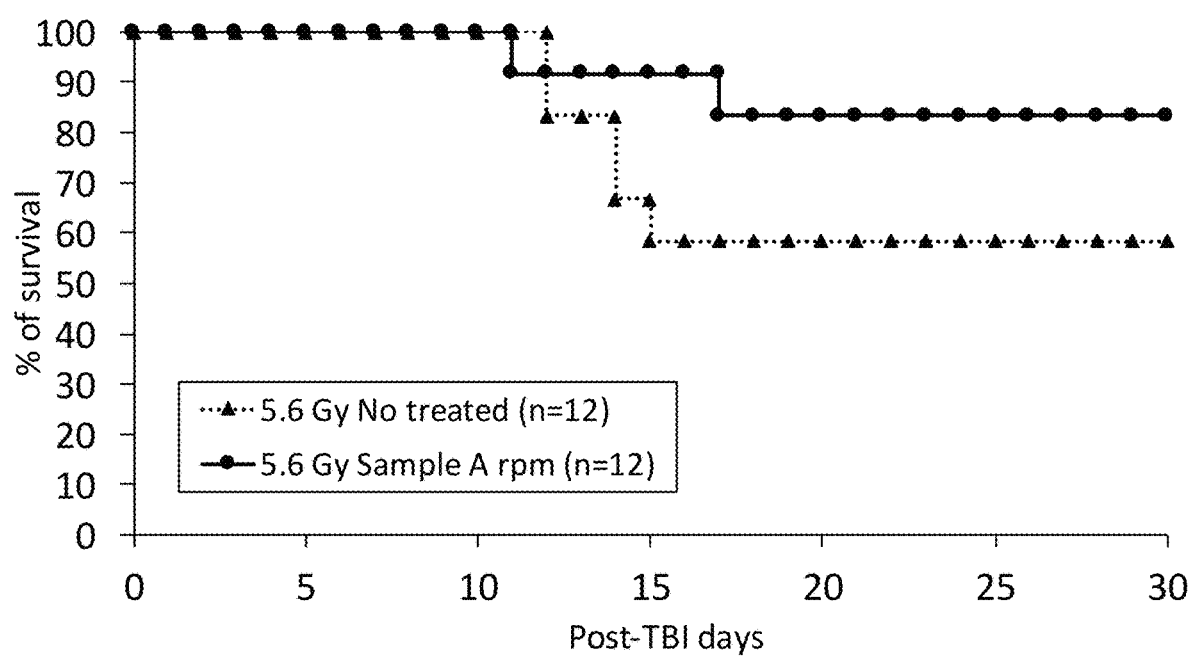
(FIG. 1A): Sample A: exemplary reverse micellar system and untreated.

The disclosure provides a reverse micellar system comprising at least a sterol, 50 to 90% of acylglycerol, 1 to 20 (e.g., 5 to 15% of lecithin), ethanol and water, wherein the weight ratio of lecithin to acylglycerol is from 0.05 to 0.4. The reverse micellar system may further comprise an active agent, such as manganese. The reverse micellar system may be used in the treatment or prevention of a cell, tissue or organ injury in a living subject due to the exposure to ionizing radiation. For example, the disclosure provides a method of treating radiation damage in a subject (e.g., exposed to radiation therapy for treatment of a disease) comprising administering to the subject a reverse micellar system described herein in an amount effective to reduce radiation-induced damage.

Reverse Micellar System

The reverse micellar system is generally a microemulsion comprising a dispersion of water-nanodroplets in oil. The dispersion is stabilized by two surfactants (acylglycerol, more preferably a diacylglycerol and lecithin) and a co-surfactant (ethanol) that are most likely at the water/oil interface. The water forms the internal phase and the hydrophobic tails of the lipids form the continuous phase. Reverse micelles containing oil(s), surfactant(s), co-surfactant(s), and an aqueous phase are also characterized as water-in-oil microemulsions. These microemulsions are thermodynamically stable and visually limpid.

In some embodiments, the reverse micellar system is a reverse phase system comprising an aqueous phase dispersed in an oil phase. The reverse-phase system may comprise reverse or reverse swollen micelles, but these may be organized in higher ordered isotropic structures such as water-in-oil microemulsion or anisotropic structures such as cubic, hexagonal, lamellar organizations.

Generally, the size of micelles is very small, such as less than 10 nm, less than 8 nm, or less than 6 nm. The size may vary with the quantity of added water and lecithin. The present invention relates more particularly to reverse micelles with an aqueous core of around 4 nm, preferably 3 to 5 nm, more preferably from 3.5 to 5 nm, in particular from 3.7 to 4.5 nm.

The ratios of the lipidic constituents (including sterol, acylglycerol and lecithin) in the reverse micellar system according to the invention can vary. For instance, the weight ratio sterol/acylglycerol can range from 0.01 to 0.1, more particularly from 0.03 to 0.07. The weight ratio lecithin/acylglycerol can range from 0.05 to 0.40, in particular from 0.06 to 0.25.

Preparation of the Reverse Micellar Systems

The reverse micellar systems described herein may be prepared by any technique known in the art. They are more particularly obtainable by the following method:

(a) contacting (i) lecithin, (ii) ethanol, (iii) sterol, (iv) acylglycerol, preferably diacylglycerol and (v) water, preferably purified water, and (b) stirring mixture obtained in step (a), at 40° C. or less, and for a time sufficient to obtain formation of the reverse micellar system.

The reverse micellar system described herein that further comprises an active agent may be prepared by any technique known in the art. They are more particularly obtainable by the following method:

(a) contacting (i) lecithin, (ii) ethanol, (iii) sterol, (iv) acylglycerol, preferably diacylglycerol, (v) water, preferably purified water, and (vi) at least one active agent, and (b) stirring mixture obtained in step (a), at 40° C. or less, and for a time sufficient to obtain formation of the reverse micellar system.

The parameters of stirring (e.g., duration and speed of mechanical stirring) can be readily determined by any one skilled in the art and depend on experimental conditions. In practice, these parameters are such that a homogenous reverse micellar system is obtained; the speed is determined so as to enable formation of a visually limpid formulation, and duration of the stirring is such that the stirring may be stopped a few minutes after obtaining the visually limpid formulation.

Components of the Reverse Micellar Systems

Lecithin

The term lecithin refers to phosphatidylcholine. Phosphatidylcholine is also known as 1,2-diacyl-glycero-3-phosphocholine or PtdCho. It is composed of a choline, a phosphate group, a glycerol and two fatty acids. It is a group of molecules, wherein the fatty acid compositions vary from one molecule to another. Phosphatidylcholine may be obtained from commercial lecithin that contains phosphatidylcholine in weight fractions from 20 to 98%. Preferably, the lecithin comprises more than 92% weight phosphatidylcholine. The lecithin used in the examples is LIPOID S100 (sold by lipoid company) and contains phosphatidylcholine at a fraction of more than 94%.

As mentioned above, the ratios of the lipidic constituents (lecithin, sterol and acylglycerol) in the reverse micelle system can vary. The weight ratio lecithin/acylglycerol can range from 0.05 to 0.40, in particular from 0.06 to 0.25. The weight of lecithin corresponds to the total weight of the mixture containing phosphatidylcholine, such as LIPOID S100 described above.

Sterols

The sterols useful for the preparation of the reverse micelle systems described herein are preferably natural sterols, such as cholesterol or phytosterols (vegetable sterols). Sitosterol and cholesterol are the preferred sterols useful for the reverse micelle systems. Preferably, the reverse micellar system comprises sitosterol, such beta-sitosterol.

Sitosterol and cholesterol are commercially available. More particularly, commercial sitosterol, which is extracted from a variety of pine called tall oil, can be used. In such a product, the sitosterol generally represents from 70 to 80% by weight of the product and is generally found in a mixture with campesterol and sitostanol in respective proportions in the order of 10% each. Commercial sitosterol which is extracted from soya can also be used.

Preferably, the weight ratio sterol/acylglycerol can range from 0.01 to 0.1, more particularly from 0.03 to 0.07. The weight of sterol corresponds to the total weight of sterols used in the formulation.

Acylglycerols

Acylglycerols useful for the preparation of the reverse micellar systems described herein can be isolated from the majority of animals and more preferably plants. Acylglycerols include mono- di and triacylglycerols. In a particular embodiment, acylglycerols preferentially used have the following formula (I):

in which:

R1 is an acyl residue of a linear or branched, saturated or unsaturated fatty acid having between 14 and 24 carbon atoms;

R2 is an acyl residue of a linear or branched unsaturated fatty acid having between 2 and 18 carbons atoms, or a hydrogen atom;

R3 is an acyl residue of a linear or branched, saturated or unsaturated fatty acid having between 14 and 24 carbon atoms, or a hydrogen atom.

According to a particular embodiment, R1 or R3, preferably only one of R1 and R3, in particular only R1, represents an acyl residue of oleic acid (C18: 1[cis]-9).

According to a particular aspect, R2 has advantageously 18 carbon atoms, preferably R2 is an oleic acid residue (oleoyl group), one of its positional isomers with respect to the double bond (cis-6, 7, 9, 11 and 13) or one of its iso-branched isomers.

According to another particular aspect, R1 represents an oleoyl group.

According to another particular aspect, R3 is a hydrogen atom.

According to another particular aspect, R2 and R3 are hydrogen atoms.

As a general rule, oil containing a high concentration of oleic acid will be chosen as a useful source of acylglycerols according to the invention. Such oil usually contains a high proportion of acylglycerols useful according to the invention.

According to a particular aspect of the invention, the preferred diglycerols of fatty acids are 1,2-dioleoylglycerol (or also named herein 1,2-diolein) and 1-oleoyl-2-acetyl glycerol.

Acylglycerols are commercially available. For instance, glycerol monooleate 40 contains about 32 to 52% of monoacylglycerol, 30 to 50% of diacylglycerol, 5 to 20% of triacylglycerol and is pharmaceutically accepted (European Pharmacopeia (9th Edition), USP 25/NF20, and Japanese Standard of food Additives).

Such product is commercially available by Gattefossé Company under the name Peceol®. In particular, Peceol® may comprise around 43 wt % of monoacylglycerol, around 44 wt % of diacylglycerol and around 11 wt % of triacyl glycerol (the acyl fraction of Peceol® is mainly made of oleoyl—usually around 80% of the acyl residue is oleoyl fraction).

The weight of acylgylycerol corresponds to the total weight of the mixture containing an acylglycerol, or a mixture of acylglycerols, with glycerol and fatty acids derived from said acylglycerol(s).

Ethanol

Ethanol is generally an ethanol-water solution, wherein the ethanol amount is from about 90% to 99% by volume. In another embodiment, ethanol is absolute or anhydrous alcohol (that refers to ethanol with a low water content). There are various grades with maximum water contents ranging from 1% to a few parts per million (ppm) levels. Absolute ethanol is preferred.

Water

The water useful for the preparation of the reverse micelle systems described herein is preferably purified water; more particularly distilled or deionized water.

Other Components

The reverse micellar systems described herein may comprise any type of additional components, such as alcohols other than ethanol.

The reverse micellar systems described herein may comprise at least one alcohol in addition to ethanol as defined above. The alcohols that may be used are preferably linear or branched mono-alcohols with two to four carbons atoms. Examples of alcohols are 1-propanol, 2-propanol, 2-methyl-1-propanol, isopropanol, and any mixture thereof. Polyols that may be used according to the invention are preferably glycerol and propylene glycol.

The amounts of the components of the reverse micellar system can be adapted depending on the desired properties for the system, such as visual appearance, viscosity, and/or concentration of active agent for instance.

In some embodiments, the amounts of the components of the reverse micellar system are adjusted so that the reverse micellar system is in the form of a liquid. A person of skill in the art can adapt the relative amounts of acylglycerol, sterol, lecithin, ethanol and water in the reverse micellar system for obtaining a liquid with the desired properties, such as visual appearance, viscosity, and/or concentration of active agent for instance.

Examples of amounts for the different components of the reverse-micellar systems are the following:

The reverse-micellar system may comprise from 1 to 20%, preferably 5 to 15% of lecithin.

The reverse-micellar system may comprise from 1 to 15%, preferably from 5 to 15% water.

The reverse-micellar system may comprise from 5 to 15% alcohols, including ethanol.

The reverse-micellar system may comprise from 0.825 to 5% sterol.

The reverse-micellar system may comprise from 50 to 90% acylglycerol.

Unless otherwise specified, the percentage values used herein are weight percentages with respect to the total weight of the reverse-micellar system. The amounts specified herein will be adapted as to correspond more specifically to the weight ratios identified above.

In some embodiments, the reverse micellar system does not comprise liposomes, nucleic acids, and/or chelating agents.

Active Agent

In some embodiments, the reverse micellar systems described herein may optionally comprise an active agent. The active agent is a compound capable of preventing and/or treating damage caused by the exposure to the ionizing radiation of any type and capable of increasing the efficiency of reverse micellar system per se.

In other embodiments, the active agent is not used for its radionuclide or metal chelating/sequestering properties. For example, in some embodiments, the reverse micellar systems described herein are free of the chelating/sequestering agents disclosed in U.S. Pub. No. 2017/0035909, hereby incorporated by reference in its entirety. For example, in some embodiments, the reverse micellar systems described herein are free of DTPA, bisphosphonates, Prussian blue, EDTA, Trientine, D-penicillamine, Deferoxamine, BAL, DMSA, DMPS, Phytic acid, Hydroxypyridonates (HOPO), mercaptoacetyltriglycine (MAG3), chelating peptides, derivatives thereof and combinations thereof.

In other embodiments, the reverse micellar systems described herein are free of the nucleic acids (e.g., DNA, RNA) described in U.S. Pat. No. 9,452,136, hereby incorporated by reference in its entirety.

In other embodiments, the reverse micellar systems described herein are free of the cyano-bridged metal nanoparticles described in WO 2017/005899, hereby incorporated by reference in its entirety.

In an embodiment, the active agent may be a compound unknown in the prior art to be useful for preventing and/or treating the damages caused by the exposure to the ionizing radiation of any type.

In another embodiment, the active agent may be a compound known in the prior art for preventing and/or treating the damages caused by the exposure to the ionizing radiation of any type but not used because of its side effects.

In some embodiments, the active agent comprises one or more of manganese, lithium, selenium, copper and/or zinc. In particular embodiments, the active agent is a pharmaceutically acceptable salt of manganese, such as manganese sulfate; a pharmaceutically acceptable salt of lithium, such as lithium citrate; a pharmaceutically acceptable salt of selenium, such as selenite sodium or selenite sulfate; a pharmaceutically acceptable salt of copper such as copper sulfate; and/or a pharmaceutically acceptable salt of zinc, such as zinc sulfate. In other particular embodiments, the reverse micellar systems described herein comprise at least 300 µg/g of manganese, or at least 500 µg/g of manganese; at least 600 µg/g of lithium; at least 100 µg/g of selenium, at least 100 µg/g of copper; and/or at least 500 µg/g of zinc. In a particular embodiment, the reverse micellar systems described herein comprise from 1,000 to 2,000 µg/g of manganese. The skilled person will be able to adapt the ratios of the components of the reverse micellar system and the amount of active agent to encapsulate any active agent into the reverse micellar system as described herein.

Subject

"Subject" refers to an organism to which the reverse micellar systems described herein can be administered. The subject may be a human or a non-human animal, such as a mammal.

Treatment

The disclosure contemplates various methods of treatment. For example, the disclosure provides methods of treating a subject from radiation damage comprising administering an effective amount of a reverse micellar system described herein to a subject who has been exposed to radiation.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as cancer.

In some embodiments, the treatment inhibits radiation damage in a subject. In other embodiments, an effective amount of a reverse micellar system described herein is administered to a subject exposed to radiation therapy for treatment of cancer. In particular embodiments, the cancer cells are more sensitive to the radiation therapy than non-cancerous cells. In other embodiments, an effective amount of a reverse micellar system described herein is administered to a subject exposed to radioisotopes for medical diagnosis. In other embodiments, an effective amount of a reverse micellar system described herein is administered to a subject after military combat. In other embodiments, an effective amount of a reverse micellar system described herein is administered to a subject after a nuclear attack or accident. In other embodiments, an effective amount of a reverse micellar system described herein is administered to a subject exposed to radiation but before symptoms of radiation damage appear.

Prevention

The disclosure contemplates various methods of prevention. For example, the disclosure provides methods of preventing a subject from radiation damage comprising administering an effective amount of a reverse micellar system to a subject at risk to radiation exposure.

"Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

In some embodiments, an effective amount of a reverse micellar system described herein is administered to a subject at risk to radiation exposure. In other embodiments, an effective amount of a reverse micellar system described herein is administered to a subject before radiation therapy (e.g., for treatment of cancer). In particular embodiments, following radiation therapy for treatment of cancer, cancer cells are more sensitive to the radiation therapy than non-cancerous cells. In other embodiments, an effective amount of a reverse micellar system described herein is administered to a subject before administering radioisotopes for medical diagnosis. In other embodiments, an effective amount of a reverse micellar system described herein is administered to a subject before the subject enters military combat. In other embodiments, an effective amount of a reverse micellar system described herein is administered to a subject before a nuclear attack or accident.

Dosage Regimen

The reverse micellar systems described herein are capable of being absorbed through mucosa. The reverse micellar system may be administered via different routes, including a transmucosal route, through buccal mucosal tissue, or permucosally.

As used herein, the terms "mucosa" and "mucosal" refer to a mucous tissue such as of the respiratory, digestive, or genital tissue. "Transmucosal delivery", "mucosal delivery", "mucosal administration" and analogous terms as used herein refer to the administration of a composition through a mucosal tissue. "Transmucosal delivery", "mucosal delivery", "mucosal administration" and analogous terms include, but are not limited to, the delivery of a reverse micellar system described herein via bronchi, gingival, lingual, nasal, oral, buccal, oesophageal, vaginal, rectal, and gastro-intestinal mucosal tissue.

The reverse micellar systems described herein may be administered at any time respect to the radiation exposure. In some embodiments, the reverse micellar systems described herein are administered before exposure to ionizing radiation, such as days before exposure to ionizing radiation. In other embodiments, the reverse micellar systems described herein are administered after exposure to ionizing radiation, such as in the first day, in the first hour, or in the first 15 minutes, following the exposure to ionizing radiation. In other embodiments, the reverse micellar systems described herein are administered more than 24 hours, more than 48 hours, or more than 96 hours after the end of the exposure to the ionizing radiation. In other embodiments, the reverse micellar systems described herein may be continued to be administered for several days or weeks after the end of the exposure to the ionizing radiation. In other embodiments, the reverse micellar systems described herein are administered before and after exposure to ionizing radiation.

As used herein, the terms radioprotection or radioprotector (rp) refer to reverse micellar systems administered prior to radiation exposure.

As used herein, the terms radiomitigation or radiomitigator (rm) refer to reverse micellar systems administered after the radiation exposure.

As used herein, the terms radioprotection/radiomitigation (rpm) refer to reverse micellar systems administered before and after the radiation exposure.

The skilled person will be able to adapt the number of daily administrations of reverse micellar system, the amount to be administered, the frequency of administration and/or the moment when the treatment is started or stopped in view of the type and intensity of the irradiation.

The skilled person will be able to adapt the number of daily administrations of reverse micellar system comprising an active agent, the amount to be administered, the frequency of administration and/or the moment when the treatment is started or stopped in view of the type and intensity of the irradiation and the amount of the active agent present in the reverse micellar systems.

The reverse micellar systems described herein may be formulated in a composition further comprising a pharmaceutically acceptable support. In some embodiments, a pharmaceutical composition comprising a pharmaceutically acceptable support and a reverse micellar system comprising an acylglycerol, lecithin, ethanol, sterol water and optionally an active agent is provided. The pharmaceutical compositions may be in the form of a capsule, a caplet, an aerosol, a spray, a solution or a soft elastic gelatin capsule.

The term "pharmaceutically acceptable support" refers to any pharmaceutically acceptable excipient, vehicle or carrier, well-known to the person skilled in the art. Other additives well-known to the person skilled in the art such as stabilizers, drying agents, binders or pH buffers may also be used in the pharmaceutical compositions described herein. In particular embodiments, excipients that promote adherence of the finished product to the mucosa are included in the pharmaceutical compositions. In other embodiments, the reverse micellar system per se or comprising an active agent may be used in combination with one or more additional agents.

Ionizing Radiation

The disclosure provides reverse micellar systems for treating and/or preventing injury from radiation, such as ionizing radiation. Ionizing radiations relates to particles or waves having sufficiently high energy to ionize an atom or a molecule in a living body. Particle radiations include alpha, beta or neutrons. Electromagnetic waves include X or γ ray.

As used herein, "radiation exposure" or "irradiation" refer to being exposed or at risk to be exposed to ionizing radiations. Ionizing radiation may result from a number of sources including, but not limited to, nuclear event, nuclear power plant accident, intentional terrorist attack with a dirty bomb, medical practice such as diagnostic nuclear imaging and therapeutic radiations.

External and internal radiation exposure refer to the location of the source of radiation. "External ionizing radiation exposure" refers to the location of the source outside of the body, whereas "internal ionizing radiation exposure" refers to the location of the source inside the body (e.g., a radionuclide inhaled, ingested or present into the bloodstream, such as after injection or through wounds).

Ionizing Damage

The extent of radiation-induced internal damages will depend on duration, dose and type of radiation exposure and on the sensitivity of different tissues and organs. Radiation side effects can be classified as either acute, occurring during or immediately after radiation exposure, or late such as fibrosis, occurring weeks to months later.

As used here, "Acute Radiation Syndrome" or ARS relates to a damage caused by whole-body or partial body irradiation in a human at high dose of penetrating radiation in a very short period of time (usually a matter of minutes). Clinical manifestations include gastrointestinal, hematopoietic, and neurovascular sub-syndromes.

In some embodiments, the radiation is potentially lethal. In other embodiments, ionizing radiations induce sequential steps of cellular, tissue, organ, and total body injury. Injury and death of cells is a combination of direct and indirect ionizing radiation damages.

The exact mechanisms of reverse micellar systems described herein to treat radiation induced damage remain unclear. Without any intention of being bound by any theory, one explanation is that reverse micellar systems described herein act on the damaged cellular membranes in the whole body. The active agent optionally comprised in the reverse micellar systems is delivered in the whole body and add their own therapeutic activity at their target sites.

EXAMPLES

Various embodiments will now be particularly described by way of examples. The following descriptions of specific embodiments are presented for purposes of illustration and description. They are not intended to be exhaustive of or to limit the disclosure.

Example 1: In Vivo Studies of the Efficacy of Reverse Micelles on Survival of Irradiated Mice at 30 Days Samples
Sample A
2.5 g of commercially available lecithin, containing more than 94% of phosphatidylcholine, was dissolved in 4.5 g of absolute ethanol under magnetic stirring at 300 r/min at room temperature. 1.2 g of phytosterol, containing more than 70% of beta-sitosterol, was added to the mixture and stirred in the same conditions. 38.7 g of Peceol® was added thereto and magnetic stirring was carried out at 700 r/min at 37° C. to form an oil mixture. 0.4 g of purified water were added to 5.6 g of the oil mixture and stirred at room temperature few minutes to form a reverse micellar system.

Sample B
0.5 g of purified water containing 13.9 mg of manganese sulfate (4.5 mg of metal manganese) was added to 8.5 g of the oil mixture described in sample A and stirred at room temperature few minutes to form a reverse micellar system comprising 500 µg of metal manganese/g or 470 µg of metal manganese/ml (density of 0.94).

Sample C
0.3 g of purified water containing 5.6 mg of manganese sulfate (1.8 mg of metal manganese) was added to 5.7 g of the oil mixture described in sample A and stirred at room temperature few minutes to form a reverse micellar system comprising 300 µg of metal manganese/g or 282 µg of metal manganese/ml (density of 0.94).

Sample D
0.4 g of purified water containing 9.3 mg of manganese sulfate (3.0 mg of metal manganese) was added to 5.6 g of the oil mixture described in sample A and stirred at room temperature few minutes to form a reverse micellar system comprising 500 µg of metal manganese/g or 470 µg of metal manganese/ml (density of 0.94).

Sample E
10.0 g of commercially available lecithin, containing more than 94% of phosphatidylcholine, was dissolved in 18.0 g of absolute ethanol under magnetic stirring at 300 r/min at room temperature. 5.0 g of phytosterol, containing more than 70% of beta-sitosterol, was added to the mixture and stirred in the same conditions. 155.0 g of Peceol® was added thereto and magnetic stirring was carried out at 700 r/min at 37° C. to form an oil mixture. 1.2 g of purified water was added to 18.8 g of the oil mixture and stirred at room temperature few minutes to form a reverse micellar system.

Sample F
1.2 g of purified water containing 31.0 mg of manganese sulfate (10.0 mg of metal manganese) was added to 18.8 g of the oil mixture described in sample E and stirred at room temperature few minutes to form a reverse micellar system comprising 500 µg of metal manganese/g or 470 µg of metal manganese/ml (density of 0.94).

Materials and Methods 3 studies, conducted in accordance with the European and French regulations for animal experimentation (European directive 2010/63/EU, Sep. 22, 2010 and French decree 2013-118, Feb. 1, 2013), are described below and in Table 1.

The animals used were male non-consanguineous Swiss CD1 mouse strain of 4.5 to 6 weeks of age at receipt in the laboratory. Mice were allowed free access to commercial diet (SSNIFF with 21% of raw proteins at the first step of life, and during experiment) distributed in food hoppers, and pre-filled acidified water bottles during acclimatization and experimentation. 6 or 12 mice form a test batch.

Mice were exposed to a vertical X-ray beam (top to bottom), at 78-79 cm from the source (FSD), in a self-protected SARRP cabin (Small Animal Radiation Research Platform, X-Strahl). They were kept vigilant, in contention in a box of Plexiglas, one individual per cage.

Total body irradiation (TBI) was calculated to be 50% (study 1), 90% (study 2) or 99.9% (study 3) lethal at day 30, i.e., $LD_{50/30}$; $LD_{90/30}$ or $LD_{99.9/30}$. A "medium" dose rate of 0.16 Gy/min (programmed intensity of 3.2 mA) was chosen. The irradiation lasted about 35 minutes and 54 seconds for a dose of 5.6 Gy output (study 1), about 39 minutes and 42 seconds for a dose of 6.2 Gy output (study 2) and about 44 minutes, for a dose of 7 Gy output (study 3). The animals being held in contention, additional stress is to be taken into consideration, very probably growing as duration of restraint increases.

The treatments (Samples A to F) were administered to mice by rectal permucosal route, using a micropipette with tips. Delivery was performed slowly in order to not hurt the animal and to cover the maximal mucosal surface. Despite this precaution, the introduction of the tips into the rectum can stimulate defecation. In case of any suspicion of loss of product by defecation within 2 to 3 minutes following the rectal injection, a second administration of the same amount (30 µl/mouse of 30 g) was made. In practice, the vast majority of animals defecated, so that the experimenter carried out a second intra rectal injection to all the animals.

The treatment was started before irradiation and continued after irradiation (rpm) or started after irradiation (rm).

Figure 1B:
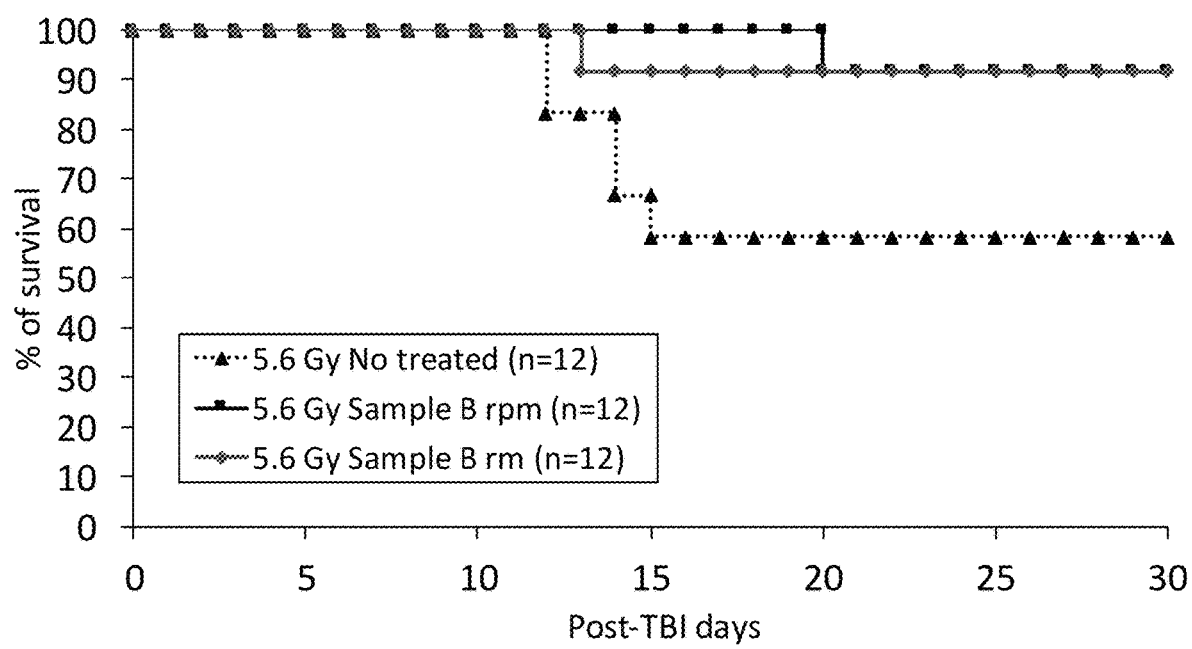
(FIG. 1B): Sample B: manganese formulated at 500 μg/g in reverse micellar system and untreated; rm=radiomitigation; rpm=radioprotection/radiomitigation.

The endpoints of the 3 studies were the percentage of mice survival at 30 days following TBI and the evolution of the survival curves during the intermediate period. The surviving mice were euthanized under isoflurane anaesthesia by decapitation at day 77 or 74 (study 1) or at day 30 (studies 2 and 3) following irradiation exposure.

reached 58% at day 30 and rose to 83% in animals treated with sample A (see FIG. 1A). The survival of animals treated with sample B (groups sample B rpm and sample B rm) was 92%, irrespective of the schedule of treatment (see FIG. 1B).

Figure 2:
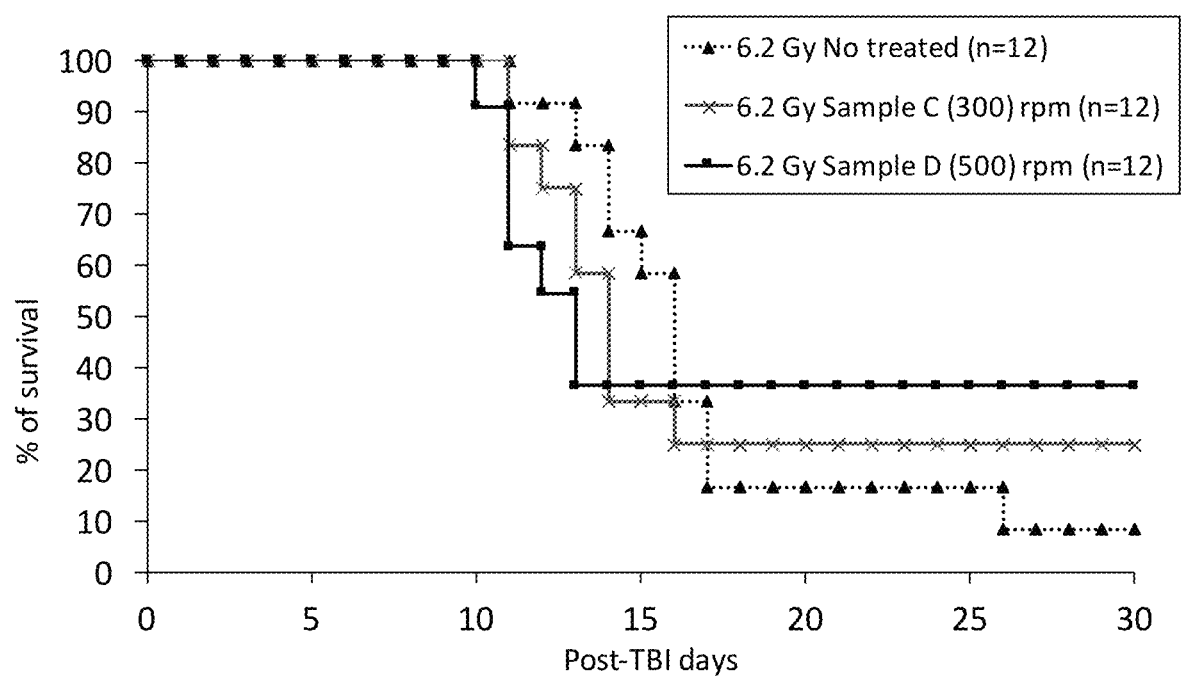
FIG. 2: Post-TBI survival in CD1 Swiss mice after a 6.2 Gy dose irradiation at 0.16 Gy/min dose rate ($LD_{90/30}$). Treatments: Sample C: manganese formulated at 300 μg/g in reverse micellar system, Sample D: manganese formulated at 500 μg/g in reverse micellar system, and untreated; rpm=radioprotection/radiomitigation.

Study 2:

Mice (n=12/group) untreated or treated were exposed to a 6.2 Gy TBI ($LD_{90/30}$). Mice were treated by rectal administration with sample C or D following the same schedule: 1 and 2 hours before TBI and 24 hours after TBI. As shown in FIG. 2, under this protocol of irradiation, untreated animals exhibited a survival of 8% and the treatment efficacy at 30 days was dependent on the dosage of manganese in the reverse micellar system: 300 µg/g in sample C or 500 µg/g in sample D, with a 25% and 33% survival respectively.

Figure 3:
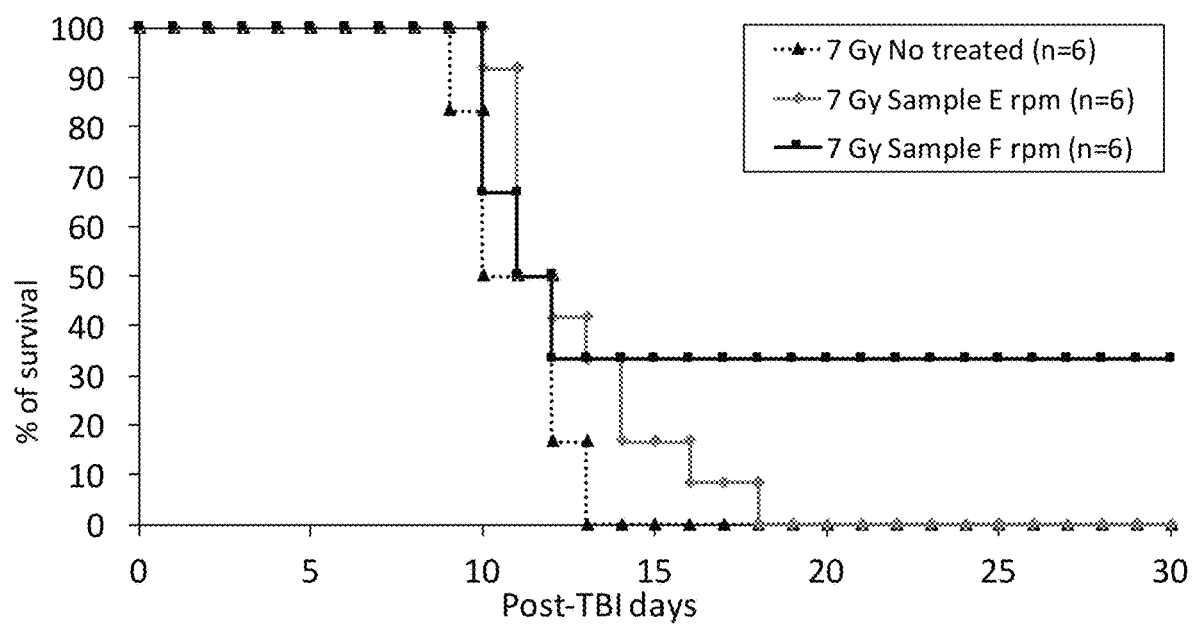
FIG. 3: Post-TBI survival in CD1 Swiss mice after a 7 Gy dose irradiation at 0.16 Gy/min dose rate ($LD_{99.9/30}$). Treatments: Sample E: exemplary reverse micellar system, Sample F: manganese formulated at 500 μg/g in reverse micellar system, and untreated; rpm=radioprotection/radiomitigation.

Study 3:

Mice (n=6/group) untreated or treated with sample E or F were exposed to a 7 Gy TBI ($LD_{99.9/30}$). Under this protocol of irradiation, mice treated by rectal administration with the reverse micellar system (group sample E), 1 and 2 hours before TBI and 0.5, 24, 48, and 96 hours following TBI, exhibited a survival at day 30 of 0% such as untreated group. However, during the intermediate period, the treatment with sample E extended the survival by 5 additional days in respect to untreated mice. Mice treated following the same schedule with manganese formulated in reverse micelles (group sample F) exhibited a survival at day 30 of 33% (see FIG. 3).

TABLE 1

| | RADIOPROTECTION | | RADIOMITIGATION | | | | | Percent survival (%) | | |
| | | | | | | | | Study 1 | Study 2 | Study 3 |
| | Time of treatment (h, t0 − irradiation) | | | | | | | $LD_{50/30\,d}$ | $LD_{90/30\,d}$ | $LD_{99.9/30\,d}$ |
| Treatments | H-2 | H-1 | H + 0.5 | H + 2 | H + 24 | H + 48 | H+96 | n = 12/group | n = 12/group | n = 6/group |
| No treatment | | | | | | | | 58 | | |
| Sample A | x | x | x | x | x | | | 83 | | |
| Sample B (Mn500) | x | x | x | x | x | | | 92 | | |
| Sample B (Mn500) | | | x | x | x | | | 92 | | |
| No treatment | | | | | | | | | 8 | |
| Sample C (Mn300) | x | x | | | x | | | | 25 | |
| Sample D (Mn500) | x | x | | | x | | | | 33 | |
| No treatment | | | | | | | | | | 0 |
| Sample E | x | x | x | | x | x | x | | | 0 |
| Sample F (Mn500) | x | x | x | | x | x | x | | | 33 |

Results

Study 1:

Mice (n=12/group) untreated or treated with sample A or B were exposed to a 5.6 Gy TBI ($LD_{50/30}$). Mice of group sample A were treated with the reverse micellar system by rectal administration 1 and 2 hours before TBI and 0.5, 2 and 24 hours after TBI. Sample B (manganese formulated in reverse micelles) was administered depending on two schedules: mice were treated by rectal administration 1 and 2 hours before TBI and 0.5, 2 and 24 hours after TBI (group sample B rpm) or were treated by rectal administration 0.5, 2 and 24 hours after TBI (group sample B rm). Under this protocol of irradiation, the survival of untreated animals

CONCLUSIONS

The overall results (summarized in Table 1) show the effectiveness of reverse micellar system per se or comprising manganese for increasing the survival rate at 30 days of treated mice as compared with untreated groups.

The survival of animals is inversely proportional to the TBI dose, a better efficacy being observed under the protocol of irradiation at $LD_{50/30}$ compared to $LD_{99.9/30}$ and $LD_{90/30}$ at the same dose rate (0.16 Gy/min). At the highest TBI dose ($LD_{99.9/30}$), the addition of manganese in the reverse micellar system prolongs beyond 30 days its intermediate effectiveness.

At $LD_{50/30}$, the efficacy of the treatment with a reverse micellar system does not depend on its starting time (i.e. before or after the irradiation).

These results suggest that reverse micellar systems described herein may be an effective medical countermeasure against severe and lethal radiation induced injuries.

Example 2: Formulations with High Concentrations of Manganese

Sample G 5.0 g of commercially available lecithin, containing more than 94% of phosphatidylcholine, was dissolved in 4.5 g of absolute ethanol under magnetic stirring at 300 r/min at room temperature. 1.2 g of phytosterol, containing more than 70% of beta-sitosterol, was added to the mixture and stirred in the same conditions. 36.3 g of Peceol® was added thereto and magnetic stirring was carried out at 700 r/min at 37° C. to form an oil mixture.

0.2 g of purified water containing 12.5 mg of manganese sulfate (4.0 mg of metal manganese) was added to 3.8 g of the oil mixture and stirred at room temperature few minutes to form a reverse micellar system comprising 1000 µg of metal manganese/g or 940 µg of metal manganese/ml (density of 0.94).

Sample H 6.0 g of commercially available lecithin, containing more than 94% of phosphatidylcholine, was dissolved in 4.5 g of absolute ethanol under magnetic stirring at 300 r/min at room temperature. 1.2 g of phytosterol, containing more than 70% of beta-sitosterol, was added to the mixture and stirred in the same conditions. 33.7 g of Peceol® was added thereto and magnetic stirring was carried out at 700 r/min at 37° C. to form an oil mixture.

0.4 g of purified water containing 25.2 mg of manganese sulfate (8.0 mg of metal manganese) was added to 3.6 g of the oil mixture and stirred at room temperature few minutes to form a reverse micellar system comprising 2000 µg of metal manganese/g or 1880 µg of metal manganese/ml (density of 0.94).

Sample I 0.4 g of purified water containing 37.7 mg of manganese sulfate (12.2 mg of metal manganese) was added to 3.6 g of the oil mixture described in sample H and stirred at room temperature few minutes to form a reverse micellar system comprising 3000 µg of metal manganese/g or 2820 µg of metal manganese/ml (density of 0.94).

Sample J 3.8 g of commercially available lecithin, containing more than 94% of phosphatidylcholine, was dissolved in 2.2 g of absolute ethanol under magnetic stirring at 300 r/min at room temperature. 0.6 g of phytosterol, containing more than 70% of beta-sitosterol, was added to the mixture and stirred in the same conditions. 15.4 g of Peceol® was added thereto and magnetic stirring was carried out at 700 r/min at 37° C. to form an oil mixture.

0.5 g of purified water containing 49.3 mg of manganese sulfate (16.0 mg of metal manganese) was added to 3.5 g of the oil mixture and stirred at room temperature few minutes to form a reverse micellar system comprising 4000 µg of metal manganese/g or 3800 µg of metal manganese/ml (density of 0.95).

Example 3: Formulations with Other Active Agents

Sample K 10.0 g of commercially available lecithin, containing more than 94% of phosphatidylcholine, was dissolved in 18.0 g of absolute ethanol under magnetic stirring at 300 r/min at room temperature. 5.0 g of phytosterol, containing more than 70% of beta-sitosterol, was added to the mixture and stirred in the same conditions. 155.0 g of Peceol® was added thereto and magnetic stirring was carried out at 700 r/min at 37° C. to form an oil mixture.

0.7 g of purified water containing 4.0 mg of selenite sulfate (1.2 mg of metal selenium) was added to 11.3 g of the oil mixture and stirred at room temperature few minutes to form a reverse micellar system comprising 100 µg of metal selenium/g or 94 µg of metal selenium/ml (density of 0.94).

Sample L 94.0 g of commercially available lecithin, containing more than 94% of phosphatidylcholine, was dissolved in 84.6 g of absolute ethanol under magnetic stirring at 300 r/min at room temperature. 23.5 g of phytosterol, containing more than 70% of beta-sitosterol, was added to the mixture and stirred in the same conditions. 647.9 g of Peceol® was added thereto and magnetic stirring was carried out at 700 r/min at 37° C. to form an oil mixture.

90.9 g of purified water containing 8.2 g of lithium citrate (0.6 g of metal lithium) was added to 850.0 g of the oil mixture and stirred at room temperature few minutes to form a reverse micellar system comprising 638 µg of metal lithium/g or 600 µg of metal lithium/ml (density of 0.94).

Sample M 3.0 g of commercially available lecithin, containing more than 94% of phosphatidylcholine, was dissolved in 5.4 g of absolute ethanol under magnetic stirring at 300 r/min at room temperature. 1.5 g of phytosterol, containing more than 70% of beta-sitosterol, was added to the mixture and stirred in the same conditions. 46.5 g of Peceol® was added thereto and magnetic stirring was carried out at 700 r/min at 37° C. to form an oil mixture.

0.1 g of purified water containing 2.8 mg of zinc sulfate (1.0 mg of metal zinc) was added to 1.9 g of the oil mixture and stirred at room temperature few minutes to form a reverse micellar system comprising 500 µg of metal zinc/g or 470 µg of metal zinc/ml (density of 0.94).

The invention claimed is:

1. A method for treatment of a subject exposed to radiation and/or preventing radiation damage in a subject at risk for exposure to radiation, comprising administering an effective amount of a reverse micellar system to said subject,
   wherein the reverse micellar system comprises at least a sterol, 50 to 90% of acylglycerol, 1 to 20% of lecithin, ethanol and water, and the weight ratio of lecithin to acylglycerol is from 0.05:1 to 0.4:1,
   wherein the reverse micellar system is free of a chelator,
   wherein the reverse micellar system is free of cyano-bridged metal nanoparticles, and
   wherein the reverse micellar system comprises at least 300 µg/g of manganese.

2. The method according to claim 1, wherein the reverse micellar system comprises 5 to 15% lecithin.

3. The method according to claim 1, wherein an effective amount of said reverse micellar system is administered to a subject at risk to radiation exposure.

4. The method according to claim 1, wherein an effective amount of said reverse micellar system is administered to a subject at risk to radiation exposure and wherein an effective amount of said reverse micellar system is administered to a subject before radiation therapy.

5. The method according to claim 1, wherein an effective amount of said reverse micellar system is administered to a subject before radiation therapy for treatment of cancer or before administering radioisotopes for medical diagnosis.

6. The method according to claim 1, wherein an effective amount of said reverse micellar system is administered to a subject before radiation therapy for treatment of cancer or before administering radioisotopes for medical diagnosis, and wherein, following radiation therapy for treatment of cancer, cancer cells are more sensitive to the radiation therapy than non-cancerous cells.

7. The method according to claim 1, wherein an effective amount of said reverse micellar system is administered to a subject at risk to radiation exposure and before said subject enters military combat.

8. The method according to claim 1, wherein an effective amount of said reverse micellar system is administered to a subject at risk to radiation exposure, and wherein said effective amount of said reverse micellar system is administered to a subject before a nuclear attack or accident.

9. The method according to claim 1, wherein an effective amount of said reverse micellar system is administered to a subject exposed to radiation.

10. The method according to claim 1, wherein an effective amount of said reverse micellar system is administered to a subject exposed to radiation and wherein said effective amount of said reverse micellar system is administered to a subject exposed to radiation therapy.

11. The method according to claim 1, wherein an effective amount of said reverse micellar system is administered to a subject exposed to radiation and wherein said effective amount of said reverse micellar system is administered to a subject exposed to radiation therapy for treatment of cancer.

12. The method according to claim 1, wherein an effective amount of said reverse micellar system is administered to a subject exposed to radiation and wherein said effective amount of said reverse micellar system is administered to a subject exposed to radiation therapy for treatment of cancer, and wherein cancer cells are more sensitive to the radiation therapy than non-cancerous cells.

13. The method according to claim 1, wherein an effective amount of said reverse micellar system is administered to a subject exposed to radiation and wherein said effective amount of said reverse micellar system is administered to a subject after military combat.

14. The method according to claim 1, wherein an effective amount of said reverse micellar system is administered to a subject exposed to radiation and wherein said effective amount of said reverse micellar system is administered to a subject after a nuclear attack or accident.

15. The method according to claim 1, wherein an effective amount of said reverse micellar system is administered to a subject exposed to radiation and wherein said effective amount of said reverse micellar system is administered to a subject exposed to radioisotopes for medical diagnosis.

16. The method according to claim 1, wherein the manganese is distributed homogeneously in all cells of the body.

17. The method according to claim 1, wherein the reverse micellar system is administered permucosally.

* * * * *